United States Patent [19]

Bernstein

[11] Patent Number: 4,486,450

[45] Date of Patent: Dec. 4, 1984

[54] METHOD OF TREATING PSORIATIC SKIN AND COMPOSITION

[75] Inventor: Joel E. Bernstein, Deerfield, Ill.

[73] Assignee: Dermalogical Enterprises, Ltd., Northbrook, Ill.

[21] Appl. No.: 167,312

[22] Filed: Jul. 14, 1980

[51] Int. Cl.³ ........................................... A61K 31/165
[52] U.S. Cl. ..................................... 424/324; 424/195
[58] Field of Search ............................... 424/324, 195

[56] References Cited

U.S. PATENT DOCUMENTS 3,880,996  4/1975  Fisher .................................. 424/184

OTHER PUBLICATIONS

Chemical Abstracts 72:53317b (1970).
Merck Index—9th Ed., 1976, p. 224, para. 1766.
Smith et al., The Journal of Investigative Dermatology, 1970, 54 (2), 170-173 (Eng.).

Primary Examiner—Leonard Schenkman
Attorney, Agent, or Firm—Ronald A. Sandler; Jerry A. Schulman

[57] ABSTRACT

A method and composition of treating psoriatic skin in which capsaicin is applied topically to the psoriatic skin in a pharmaceutically acceptable carrier wherein capsaicin is present in therapeutically acceptable concentrations of between about 0.01 and about 1 percent by weight. Subsequent exposure of the treated psoriatic skin to ultraviolet light in small doses aids treatment.

10 Claims, No Drawings

METHOD OF TREATING PSORIATIC SKIN AND COMPOSITION

BACKGROUND OF THE INVENTION

Psoriasis is a common chronic skin condition for which exist today a limited number of modestly effective agents, these being primarily topical corticosteroids and coal tar preparations. Various topical steroids effectively used to treat psoriasis of the skin includes fluocinolone acetonide, flurandrenolide, and triamcinolone acetonide are usually applied as creams or ointments. These topical steroids are most effective if covered with a polyethylene film which preferably is sealed with tape. Thin polyethylene gloves are used for treating the hands and fingers. Treatment of psoriatic skin can also include daily removal of the scales by applying soap and water and scraping gently with a soft brush, followed by the application of a keratolytic ointment.

I have observed psoriasis seems to be much less common in Mexicans and Orientals than in American Caucasians and Blacks. Mexicans and Orientals eat substantially more spicy food containing red pepper than either Caucasians or Blacks. Capsaicin (the active principle in red pepper that makes the red pepper hot) has been found to be an effective treatment for psoriasis of the skin when applied topically in divided doses. Exposure of the treated psoriatic skin to small doses of ultraviolet light also assists treatment.

SUMMARY OF THE INVENTION

The present invention relates to a method of treating psoriatic skin and a composition therefor in which capsaicin is used as the principle therapeutic agent.

An important object of the present invention is to provide a method of treating psoriatic skin in human patients in need of such treatment comprising applying to the psoriatic skin a composition containing a therapeutically effective amount of capsaicin.

Another object of the present invention is to provide a method of treating psoriatic skin in human patients in need of such treatment comprising applying to the psoriatic skin a therapeutically effective amount of capsaicin and thereafter exposing the psoriatic skin to ultraviolet light.

A further object of the present invention is to provide an antipsoriatic composition comprising a pharmaceutically acceptable carrier and a therapeutically effective amount of capsaicin.

DETAILED DESCRIPTION OF THE PREFERRED EMBODIMENT

In the practice of the present invention, capsaicin is distributed according to known techniques in various pharmaceutically acceptable carriers such as emulsions, solutions, suspensions including lotions, creams and ointments. Some of these carriers contain volatile diluents such as alcohol, glycol and the like and also may contain wetting agents, emulsifying and suspending agents.

Capsaicin the active ingredient in the psoriasis preparation is a pungent principle in fruit of the various species of Capsicum or Solanaceae (pepper plants). Chemically, Capsaicin is known as trans-8-methyl-N-vanillyl-6-nonenamide or (E)-N-[(4-hydroxy-3-methoxyphenyl)-methyl]-8-methyl-6-nonenamide. Its structure is:

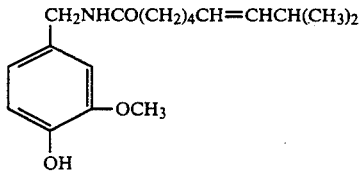

Capsaicin, commercially available from the Sigma Chemical Company, is preferably present in the pharmaceutically acceptable carrier in an amount of not less than 0.01 percent by weight and is preferably present in the range of from about 0.01 percent by weight to about 1 percent by weight.

If capsaicin is present in the pharmaceutically acceptable carrier in an amount less than about 0.01 percent by weight, then there is insufficient concentration of the capsaicin to provide effective therapy. If the capsaicin is present in an amount greater than about 1 percent by weight of the pharmaceutically acceptable carrier, then the reaction of the psoriatic skin to the topical application is too painful. I have found the initial treatment of psoriatic skin with capsaicin results in an intense red painful reaction but the psoriatic skin becomes quite tolerant to capsaicin applications upon subsequent treatment.

After treatment of patients with capsaicin in a pharmaceutically acceptable carrier, exposure to small amounts of ultraviolet light in the range of between about 3 to 5 MED per exposure in some cases hastens clearing and produces a better therapeutic benefit than the use of capsaicin alone. MED stands for "Minimum Erythemal Dose", see the Handbook of Nonprescription Drugs, Sixth Edition, American Pharmaceutical Association, 1979. The capsaicin is preferably administered topically in divided doses 2 to 4 times a day with partial clearing of the psoriasis being observable in a five to ten day range.

The following examples further illustrate the present invention:

EXAMPLE 1

An ointment containing 0.01% by weight capsaicin was applied twice daily to the abdomen by a 28 year old white patient with extensive psoriasis involving most of the body. A plain emollient ointment was applied to the other areas of the skin. Within seven days of treatment the abdomen was nearly clear of psoriatic lesions, while the rest of the body was unchanged.

EXAMPLE 2

A 0.05% by weight capsaicin solution was applied to psoriatic elbow lesions of a 30 year old white patient with mild psoriasis limited to the elbows. The solution was applied 2 to 3 times daily. The patient was first observed again two weeks later and the elbows were completely clear of psoriatic lesions.

EXAMPLE 3

A cream having 0.1% by weight capsaicin was applied 3 times a day by a 25 year old white patient with psoriasis affecting primarily the extensor surfaces of the arms and legs. Within 7 days of application redness had decreased dramatically, scaling was reduced and the lesions had decreased significantly in size.

EXAMPLE 4

A 1% by weight solution of capsaicin was prepared in an aqueous/alcohol vehicle and applied 4 times daily to the arms, legs, chest and back of a 58 year old black patient with psoriasis. Almost complete resolution of the psoriatic lesions was observed after 5 days of such treatment.

EXAMPLE 5

A cream containing 0.1% by weight capsaicin was applied 4 times daily to the arms of a 49 year old white patient with psoriasis over the extensor surfaces of both arms. One arm was exposed to ultraviolet light for from 2 to 5 minutes in increasing doses every day for 8 days using a hot quartz lamp as the source of the ultraviolet light. After 8 days both arms were significantly improved. However, the arm exposed to ultraviolet light was completely clear of psoriatic lesions, while the other arm still had some small lesions.

EXAMPLE 6

A 0.5% by weight capsaicin ointment was applied twice daily by a 42 year old black patient with psoriasis involving the arms, legs, back, abdomen, and buttock. After 1 week the patient showed significant clearing of the lesions and at this time exposure to small (2–3 minutes) of ultraviolet light was initiated daily with resulting total clearing noted by the end of the following week.

It will be apparent to those skilled in the art that only the preferred embodiments have been described by way of exemplification and that there are various modifications and alterations therein which fall in the scope of this invention and are intended to be covered by the claims appended hereto.

What is claimed is:

1. A method of treating psoriatic skin in human patients in need of such treatment comprising applying to the psoriatic skin a therapeutically effective amount of capsaicin.

2. The method of claim 1, wherein the capsaicin is present in a pharmaceutically acceptable carrier and in an amount not less than about 0.01 percent by weight of the carrier.

3. The method of claim 1, wherein the capsaicin is present in the carrier in the range of from about 0.01 percent to about 1 percent by weight of the carrier.

4. The method of claim 1, wherein the capsaicin is applied topically in divided doses.

5. A method of treating psoriatic skin in human patients in need of such treatment comprising applying to the psoriatic skin a therapeutically effective amount of capsaicin, and thereafter exposing the psoriatic skin to ultraviolet light.

6. The method of claim 5, wherein the capsaicin is present in a pharmaceutically acceptable carrier and in an amount not less than about 0.01 percent by weight of the carrier.

7. The method of claim 6, wherein capsaicin is present in the carrier in the range of from about 0.01 percent to about 1 percent by weight of the carrier.

8. The method of claim 5, wherein the amount of ultraviolet light per exposure is in the range of from about 3 MED to about 5 MED.

9. An antipsoriatic composition comprising a pharmaceutically acceptable carrier of a cream or ointment and capsaicin present in an amount not less than about 0.01 percent by weight of the carrier.

10. The composition of claim 9, wherein said capsaicin is present in the range of from about 0.01 to about 1 percent by weight of said carrier.

* * * * *

REEXAMINATION CERTIFICATE (3580th)
United States Patent [19]
Bernstein

[11] B1 4,486,450
[45] Certificate Issued Jul. 28, 1998

[54] METHOD OF TREATING PSORIATIC SKIN AND COMPOSITION

[75] Inventor: Joel E. Bernstein, 600 Knightsbridge Pkwy., Lincolnshire, Ill. 60069

[73] Assignee: Joel E. Bernstein, Lincolnshire, Ill.

Reexamination Requests:
No. 90/004,043, Dec. 11, 1995
No. 90/004,731, Aug. 28, 1997

Reexamination Certificate for:
Patent No.: 4,486,450
Issued: Dec. 4, 1984
Appl. No.: 167,312
Filed: Jul. 14, 1980

[51] Int. Cl.⁶ ............................................. A61K 31/165
[52] U.S. Cl. ............................................. 514/627; 514/863
[58] Field of Search ............................ 514/627, 863

[56] References Cited

FOREIGN PATENT DOCUMENTS 56637  1/1969  Poland.

OTHER PUBLICATIONS

Krüger, *Determination of Capsaicin in Dried Plants and Galenic Preparations* [translated title] (1956) (Inaugural–Dissertation zur Erlangung der Doktorwurde, Freien Universitat Berlin), together with a translation.

Schulte & Krüger, *Observations on the Influence of the Properties of Ointment Base on the Effectiveness of Ointments Containing Capsaicin* [translated title], 27 Mitt. Deutsch. Pharm. Ges. 172–176 (1957), together with a translation.

Molnar,, *Pharmacological Effects of Capsaicin, The Pungent Active Ingredient of Paprika* [translated title], 15 Arzneimittel Forschung 718 (1965), together with a translation.

Swift, Bernstein, Soltani & Lorincz, *Inhibition of Axon Reflex Vasodilatation in Human Skin by Topically Applied Capsaicin*, 27 Clinical Research, 245A (1979) (abstract).

Schulte & Krüger, *Influence of the Ointment Base on the Activity of Capsaicin–Containing Ointments*, Chemical Abstracts 52:2334i (1958).

External Analgesic Drug Products for Over–The–Counter Human Use, 44 Fed. Reg. 69768 (1979) (proposed Dec. 4, 1979).

United States Dispensatory, J.B. Lippincott Company, p. 242 (Arthur Osol & George E. Farrar, eds., 25th ed. 1960).

M.R. Srinivasan, M.N. Satyanarayana & M.V.L. Rao, *A Thin Layer Chromatographic Method for the Estimation of Capsaicin and Related Compounds*, 26 Research & Indust. 180 (1981).

T. Altinkurt, *Determination of Capsaicin in Oleoresin and Fruit of Capsicum*, 22 Eczacilik Bul. 22 (1980).

V.S. Govindarajan, S. Narasimhan & S. Dhanarus, *Evaluation of Spices and Oleoresins. II Pungency of Capsicum by Scoville Heat Units—A Standardized Procedure*, 14 J. Food Sci. & Tech. 28 (1977).

The Merck Index, Merck & Co. (M. Windholz ed., 9th ed. 1976).

K. Lee, T. Suzuki, M. Kobashi, K. Hasegawa & K. Iwai, *Quantitative Microanalysis of Capsaicin, Dihydrocapsaicin and Nordihydrocapsaicin Using Mass Fragmentography*, 123 J. Chromatography 119 (1976).

H.T. Behrman, *The Scalp in Health & Disease* (1952).

*Primary Examiner*—Kimberly R. Jordan

[57] ABSTRACT

A method and composition of treating psoriatic skin in which capsaicin is applied topically to the psoriatic skin in a pharmaceutically acceptable carrier wherein capsaicin is present in therapeutically acceptable concentrations of between about 0.01 and about 1 percent by weight. Subsequent exposure of the treated psoriatic skin to ultraviolet light in small doses aids treatment.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–8 is confirmed.

Claim 10 is cancelled.

Claim 9 is determined to be patentable as amended.

9. An antipsoriatic composition [comprising] *consisting essentially of* a pharmaceutically acceptable *cream* carrier [of a cream or ointment] and capsaicin present in an amount [not less than about 0.01] *greater than 0.01 percent and less than 0.1* percent by weight of the carrier *wherein said amount provides effective therapy after topical application to the skin.*

* * * * *